United States Patent [19]

Mackles et al.

[11] Patent Number: 5,587,152
[45] Date of Patent: Dec. 24, 1996

[54] CLEAR SOLID TOPICAL DEODORANT COMPOSITIONS COMPRISING A WATER-INSOLUBLE ESTER OF A WATER-SOLUBLE ACID

[76] Inventors: Leonard Mackles, 311 E. 23rd St., New York, N.Y. 10010; Leonard Chavkin, R.R. 1, Box 90, Bloomsbury, N.J. 08804

[21] Appl. No.: 444,443

[22] Filed: May 19, 1995

Related U.S. Application Data

[63] Continuation-in-part of Ser. No. 357,107, Dec. 15, 1994, abandoned.

[51] Int. Cl.$^6$ .................................................. A61K 7/32
[52] U.S. Cl. ........................ 424/65; 424/400; 424/401; 512/1
[58] Field of Search ....................... 424/65, 66, 67, 424/400, 401, 68; 512/1; 556/27, 34, 134

[56] References Cited

U.S. PATENT DOCUMENTS

| | | | |
|---|---|---|---|
| 5,463,098 | 10/1995 | Giovanniello et al. | 424/66 |
| 5,490,979 | 2/1996 | Kasat et al. | 424/66 |

*Primary Examiner*—Terressa Mosley
*Attorney, Agent, or Firm*—Omri M. Behr, Esq.

[57] ABSTRACT

A clear solid topical deodorant composition comprising 50 to 98% by weight of at least one water-insoluble ester of a water-soluble acid having solubility in water of greater than 50% w/w at 20° C., 2 to 6% by weight of dibenzylidine sorbitol, 0 to 44% by weight of one or more optional ingredients, said composition being substantially free of water and of water-miscible solvents which are liquid at ambient temperature. In one embodiment, the water-insoluble liquid ester is present at 85–98% by weight of the composition.

10 Claims, No Drawings

CLEAR SOLID TOPICAL DEODORANT COMPOSITIONS COMPRISING A WATER-INSOLUBLE ESTER OF A WATER-SOLUBLE ACID

This application is a continuation in part of U.S. patent application Ser. No. 08/357,107 by Mackles et at. filed Dec. 15, 1994 now abandoned.

FIELD OF THE INVENTION

Improved clear solid compositions, substantially free of water, for topical application and delivery of a deodorant effect to the skin, optionally further comprising additional active compounds, and further imparting a pleasant skin feel.

BACKGROUND OF THE INVENTION

Underarm odor is the result of attack by microorganisms upon the excretion products of the sweat glands and sebaceous glands in the skin. There are two types of sweat glands in the underarm, i.e., eccrine and apocrine. Eccrine glands are numerous and secrete a clear aqueous sweat directly onto the skin surface, thereby serving a thermoregulatory function. The secretions of eccrine glands are not responsible for underarm odor except that they provide a warm, moist environment which encourage the growth of microorganisms. Apocrine glands, which are larger and fewer, are usually associated with sebaceous glands. The function of these glands is not understood, but their milky secretions contain nutrients for microorganisms. It is believed that the characteristic underarm odor is produced by the odorous products of microorganisms, and by the action of esterases, elaborated upon the skin by microorganisms, upon apocrine secretions Underarm odor can be controlled in a variety of ways. Washing of the underarms controls odor only if washings are repeated throughout the day. Such repeated washing is not practicable; consequently, practically all adults in this country use a topical product to control underarm odor.

There are two classes of topical products which are effective in controlling underarm odor, i.e., antiperspirants and deodorants. Antiperspirants work by reducing the flow of eccrine perspiration to reduce wetness in the underarm area and by inhibiting the growth of microorganisms. Antiperspirant compositions are conventionally available in aerosol, roll-on and stick product forms. Clear antiperspirants typically comprise an antiperspirant active such as aluminum hydroxy chloride in a solvent, typically a lower monohydric alcohol or lower polyglycol, plus a gelling agent. Due to their acidic pH, these antiperspirant compositions inhibit microorganism growth and also chemically neutralize the odorous products formed by these microorganisms.

(Dibenzylidine sorbitol ("DBS"), a gelling agent which has been conventionally used to gel clear cosmetic compositions such as antiperspirants, is stable in alkaline neutral or slightly acidic compositions. In additions to gelling, or solidifying, topical compositions, DBS frequently imparts transparency or translucency to these compositions).

Despite their microorganism-inhibiting acidity, conventional antiperspirant compositions have been found to have numerous shortcomings. The most siw~yvysant shortcoming is that the antiperspirant active may irritate the skin of some users. Furthermore, when non-volatile glycols, for example, propylene glycol, are used as the solvent, the composition can impart an unpleasant stickiness to the skin. When components of the solvent are volatile, these components may evaporate during storage, leading to a drying of the composition or even to physical shrinkage in the product's size. Further, these compositions typically must include a stabilizer ingredient. Finally, high temperatures are required to solubilize dibenzylidine sorbitol as the gelling agent in certain formulations.

Deodorant compositions, also available in aerosol, roll-on and stick product forms, typically comprise an antimicrobial agent to inhibit the growth of microorganisms and a fragrance to mask odor. Conventional deodorant active ingredients include bacteriostatic quaternary ammonium compounds such as cetyl trimethyl-ammonium bromide and benzalkonium chloride, as well as zinc salts such as zinc citrate. In deodorant stick compositions, the antimicrobial agent and fragrance are carried in a low volatility solvent, such as propylene glycol, and solidified by a gelling agent such as a soap. DBS is a suitable alternative gelling agent. When DBS is so used, deodorant compositions further include an emollient such as di-n-butyl-phthalate and a polar solvent such as ethanol, as described in U.S. Pat. No. 4,816,261.

These conventional deodorant compositions have several shortcomings. The glycol and soap in these compositions create an unpleasant sticky feel on the skin. To retain their solidity, the conventional deodorant compositions must have an alkaline pH, because soap compounds are chemically stable only in alkaline formulations. Consequently, conventional deodorant compositions do not impart an acidic pH to the skin, and so are unable to exploit the benefits of an acidic composition, i.e., inhibiting microorganism growth and chemically neutralizing the odorous products of microorganisms. Further, the antimicrobial actives of several deodorants have been found to irritate the skin of a significant number of users. As with antiperspirant compositions described above, the presence of volatile solvents can lead to drying and shrinking of the solid composition upon storage. Moreover, when the gelling agent is DBS, a high heat of processing (i.e., up to 170° C.) is necessary. The presence of phthalate esters as emollients in deodorant compositions solidified by DBS also requires high processing temperatures, e.g., 170° C., to fully dissolve and disperse all components through the solvent. Still further, when the deodorant composition includes a phthalate ester as an emollient, there is the possibility of imparting a toxic effect to the skin from these esters. The resulting gels also are easily fractured and are opaque instead of clear. Finally, the deodorant effect from conventional deodorant compositions is short lived.

Certain esters of low molecular weight, water soluble acids such as hydroxycarboxylic acids, are known to have the ability to reduce the growth of microorganisms on the skin. Examples of such esters are glyceryl triacetate and triethyl citrate. Without in any way restricting the invention, it is believed that esterases elaborated by microorganisms on the skin hydrolyze the water-insoluble esters, when such esters are applied topically, to release water soluble acids. The resulting lowered skin pH inhibits the growth of the microorganisms and chemically neutralizes odorous products of microorganisms and of the action of bacterial esterases on apocrine secretions. The ability of microorganisms to produce underarm odor is thus reduced. Although the skin's natural buffering ability eventually neutralizes these acids and esterases again become active, the hydrolysis of the remaining esters on the skin again lowers skin pH to inactivate the esterases and prevent or delay development of unpleasant odor. Optionally, these esters of water soluble acids may be delivered to the skin with an anti-oxidant to enhance the deodorant effect, as described in Cosmetics and Toiletries, 95, July 1980, 48–50.

It would be desirable to produce a solid topical deodorant composition which produces an acid pH on the skin. Such a composition would allow one to exploit the inhibition of microorganism growth and chemical neutralyzation of odorous products which an acidic pH causes. It would additionally be desirable that this deodorant composition produce no unpleasant skin feel, not dry out, and not require the presence of co-solvents or stabilizing agents therein or the use of high processing temperatures in its manufacture. Finally, because consumers have exhibited a strong preference for clear (i.e., transparent or translucent) cosmetic compositions, including deodorant compositions, it would be desirable for this deodorant composition to be clear.

SUMMARY OF THE INVENTION

It has now been found that by combining a high level of certain water-insoluble esters of water-soluble acids with DBS in a composition which is substantially free of water and of water-miscible solvents which would be liquid at ambient temperature, there is produced a clear solid topical deodorant composition. Replacing conventional deodorant solvents and gelling agents with the water-insoluble esters and DBS respectively, produces a clear solid topical deodorant composition which generates the acidic pH advantage of antiperspirant compositions without the disadvantages of conventional deodorant compositions.

The presence of the clear solid topical deodorant composition at a high level produces a topical acidic pH when the one or more water-insoluble esters hydrolyzes on the skin. This topical acidic pH inhibits bacterial esterases and neutralizes the odorous products of microorganisms. Further, due to the absence of the conventional active ingredients of deodorant or antiperspirant compositions, as well as of phthalate ester emollients, the possibility of skin irritation or toxicity is virtually eliminated. The solid topical deodorant composition is also clear and thus significantly more attractive to the consumer than conventional white, opaque products. The clear solid topical deodorant composition further imparts a pleasant, soft feel to the skin, rather than an unpleasant stickiness. Producing the composition requires heating its components at significantly lower temperatures than manufacturing conventional deodorant compositions. Finally, although the composition as formulated is substantially free of water and of water-miscible solvents, it is not necessary to exclude all water from the final product. The clear solid topical deodorant composition needs no packaging barriers to water vapor, or desiccants. Instead, there may be up to approximately 3% by weight of water in the composition before the advantages described are reduced or lost.

This clear solid topical deodorant composition comprises 50 to 98% by weight of at least one water-insoluble ester of a water-soluble acid having solubility in water of greater than 50% w/w at 20° C., 2 to 6% by weight of dibenzylidine sorbitol ("DBS"), and 0 to 44% by weight of one or more optional ingredients. The composition is substantially free of water or water-miscible solvents which are liquid at ambient temperature.

The water-soluble acid may suitably be selected from the group consisting of acetic, propionic, butyric, citric, tartaric, adipic, malic and maleic acids. The at least one water-insoluble esters which produce an acidic topical pH when hydrolyzed upon the skin is selected from the group consisting of one of said water-soluble acids esterified with a low molecular weight alcohol selected from the group consisting of ethanol, propanol, isopropanol, glycerol, propylene glycol, butylene glycol and dipropylene glycol.

One embodiment of the clear solid topical deodorant composition comprises a single water-insoluble ester. In another, the one or more water-insoluble ester is present at 85 to 98% by weight and the one or more optional ingredients is present at 0 to 5% by weight.

Suitable water-insoluble esters include triethyl citrate, glyceryl triacetate, tributyl citrate, and glyceryl tripropionate, and water-insoluble liquid esters.

The limited water solubility of the esters of water soluble acids is important to the clear solid topical deodorant compositions. Water soluble solvents such as lower aliphatic alcohols (e.g., ethanol) are volatile, causing the product to dry out on storage. Non-volatile glycols such as propylene glycol leave sticky, inelegant residues on the skin. However, the esters of water soluble acids having limited water solubility are not sticky upon application to moist underarms, but leave a pleasant soft feel on the skin in addition to providing long lasting deodorant activity.

The optional ingredients of the clear solid topical deodorant composition are selected from the group consisting of coloring agents, fragrances, antimicrobial agents, topical anesthetics, topical analgesics, anti-oxidants, sunscreens and insect repellents. In a further embodiment, the clear deodorant composition may be employed as a cosmetic/therapeutic topical composition when the one or more active ingredients are selected from the group consisting of topical anesthetics, topical analgesics, anti-oxidants, sunscreens and insect repellents.

In another embodiment, the clear solid topical deodorant composition comprises 96% by weight of triethyl citrate, 3% by weight of DBS, 0.25% by weight of a topical antimicrobial agent, and 0.75% by weight of a fragrance. In a further embodiment, this composition comprises 50% by weight of triethyl citrate, 46.50% by weight of glyceryl tripropionate, 2.5% by weight of DBS, and 1.00% by weight of fragrance.

There is further provided a method of making the clear solid topical deodorant composition described above. The steps of this method comprise forming a liquid phase comprising the one or more water-insoluble esters of a water soluble acid having solubility in water of greater than 50% w/w at 20° C., and the optional ingredients, if any; heating this liquid phase to 100° C.; slowly adding DBS to this liquid phase with vigorous agitation; agitating the resulting mixture for 10 to 30 minutes while maintaining the liquid phase temperature in the range of 100° to 140° C. until a clear solution results; cooling this clear solution to 80° to 90° C. while stirring and adding in any remaining ingredients; and pouring the clear solution into molds.

DETAILED DESCRIPTION OF THE PREFERRED EMBODIMENTS

The at least one water-insoluble ester of water-soluble acids which acts as the solvent as well as the deodorizing active ingredient of the clear solid topical deodorant compositions have the following properties. They are water-insoluble esters of low molecular weight water soluble acids, such as hydroxy carboxylic acids. The water-insoluble esters are less than 10% soluble by weight in water at 20° C. Suitable water-insoluble esters include triethyl citrate, glyceryl triacetate, tributyl citrate and glyceryl tripropionate. Further suitable water-insoluble esters include those which are liquid at ambient temperature. It is noted that esters of phthalate compounds are not considered suitable for the present composition due to the possibility that they may impart toxicity to the skin. The one or more water-insoluble ester is present in the clear solid topical deodorant compositions at from 50 to 98% by weight or alternatively at from 85 to 98% by weight. With these high levels of water-insoluble ester, the clear solid topical deodorant composition delivers to the skin a substantial amount of deodorant active ingredient.

The gelling agent of the present composition is DBS. One commercially available DBS is Millithix 925 produced by Milliken Chemical of Spartanburg, S.C., USA. DBS may be incorporated in the composition at from 2 to 6% by weight. At less than about 2% by weight, the DBS is considered to impart insufficient gelling activity, so that the composition is considered insufficiently hard for spreading on the skin. Amounts of DBS greater than 6% by weight do not significantly improve the composition. Accordingly, amounts of DBS above 6% by weight in the clear solid topical deodorant compositions are considered superfluous.

The clear solid topical deodorant compositions are substantially free of water and of water-miscible solvents which are liquid at ambient temperature. By "substantially free of water," it is understood that these compositions have no more than 3% by weight of water therein. Similarly, there is no more than approximately 3% by weight of water-miscible solvents which are liquid at ambient temperature in the clear solid topical deodorant composition. Since water up to the 3% by weight level is permissible in the present composition, it is not necessary during manufacturing or storage of the clear solid topical deodorant composition to take steps to preclude water or water vapor from entering the composition or employ packaging which seals out water vapor.

The clear solid topical deodorant compositions are "clear" and "solid", as these terms are understood by persons skilled in the art; that is, these compositions are transparent or translucent, and are sufficiently hard to maintain their shape, without cracking of shattering, when spread over the skin.

One embodiment of the clear solid topical deodorant composition consists essentially of 50 to 98% by weight of one or more water-insoluble esters of watersoluble acids, 2 to 6% by weight of dibenzylidine sorbitol, and 0 to 44% by weight of one or more optional ingredients, said composition being substantially free of water or water-miscible solvents which are liquid at ambient temperature.

Among the optional ingredients suitable for inclusion in the clear solid topical deodorant composition are coloring agents, fragrances, antimicrobial agents, topical anesthetics, topical analgesics, antioxidants, sunscreens and insect repellents. One or more of each of these optional ingredients may be present in the composition. Coloring agents and fragrances suitable for the composition are those known to persons skilled in the art. The antimicrobial agents considered suitable for inclusion in the clear composition are those conventionally used in deodorant compositions. The topical anesthetics (e.g., benzocaine), topical analgesics (e.g., methyl salicylate), antioxidants (e.g., vitamin E), sunscreens and insect repellents which are suitable for the composition are those considered suitable by persons skilled in the art. It is further understood that the amount of these optional ingredients to be included in the composition is the amount that is considered suitable by persons skilled in the art.

Unlike conventional methods for manufacturing deodorant compositions, the method disclosed herein uses processing temperatures of no more than 100° to 150° C., or 100° to 140° C. It is particularly noted that the step of adding the DBS to the liquid phase in this method is to be performed slowly. If the DBS is added quickly, it may clump and so require an extended time in which to be dispersed through the liquid phase.

EXAMPLE I

| Deodorant Stick: | % w/w |
| --- | --- |
| Triethyl Citrate | 95.75 |
| DBS | 3.00 |
| Triclosan | 0.25 |
| Fragrance | 1.00 |
| | 100.00% |

EXAMPLE II

| Deodorant Stick: | % w/w |
| --- | --- |
| Triethyl Citrate | 50.00 |
| Glyceryl Tripropionate | 46.50 |
| DBS | 2.50 |
| Fragrance | 1.00 |
| | 100.00% |

EXAMPLE III

| Antifungal Stick: | % w/w |
| --- | --- |
| Tolnaftate | 1.0 |
| Glyceryl Triacetate | 95.5 |
| DBS | 3.5 |
| | 100.0% |

EXAMPLE IV

| Topical Anesthetic: | % w/w |
| --- | --- |
| Benzocaine | 20.0 |
| Triethyl citrate | 76.0 |
| DBS | 4.0 |
| | 100.0% |

EXAMPLE V

| Topical Analgesic: | % w/w |
| --- | --- |
| Menthol | 16.0 |
| Triethyl citrate | 80.0 |
| DBS | 4.0 |
| | 100.0% |

EXAMPLE VI

| Topical Analgesic: | % w/w |
| --- | --- |
| Methyl salicylate | 10.0 |
| Menthol | 16.0 |
| Triethyl citrate | 70.0 |
| DBS | 4.0 |
| | 100.0% |

The compositions of Examples I–VI above are made according to a process comprising the following steps:

A. heating a liquid phase (water-insoluble ester plus optional ingredients) to 100° C.;

B. adding the DBS, with vigorous agitation, by slowly sifting the DBS into the vortex of the liquid;

C. agitating the resulting solution for 10 to 30 minutes at temperatures in the range 100°–140° C. until the solution is clear;

D. cooling the solution with stirring to 80°–90° C. then mixing them to dissolve; and E. pouring the cooled solution into stick molds and cooling it there.

The invention now being fully described, it will be apparent to one of ordinary skill in the art that many changes and modifications may be made thereto without departing from the spirit or scope of the invention as set forth herein.

We claim:

1. A clear solid topical deodorant composition comprising:

50 to 98% by weight of at least one water-insoluble ester of a water-soluble acid having solubility in water of greater than 50% w/w at 20° C., 2 to 6% by weight of dibenzylidine sorbitol, and 0 to 44% by weight of one or more optional ingredients, said composition being substantially free of water and of water-miscible solvents which are liquid at ambient temperature.

2. A clear solid topical deodorant composition comprising:

50 to 98% by weight of at least one water-insoluble ester of a water-soluble acid having solubility in water of greater than 50% w/w at 20° C., 2 to 6% by weight of dibenzylidine sorbitol, and 0 to 44% by weight of one or more optional ingredients, said composition being substantially free of water and of water-miscible solvents which are liquid at ambient temperature, wherein said water-soluble acid is selected from the group consisting of acetic, propionic, butyric, citric, tartaric, adipic, malic and maleic acids, and said at least one water-insoluble ester is selected from the group consisting of one of said water-soluble acids esterified with a low molecular weight alcohol selected from the group consisting of ethanol, propanol, isopropanol, glycerol, propylene glycol, butylene glycol and dipropylene glycol.

3. The clear solid topical deodorant composition according to claim 1 comprising a single water-insoluble ester.

4. The clear solid topical deodorant composition according to claim 1, wherein said one or more water-insoluble esters is present at 85 to 98% by weight and said one or more optional ingredients is present at 0 to 5% by weight.

5. The clear solid topical deodorant composition of claim 2, wherein said one or more water-insoluble ester is selected from the group consisting of triethyl citrate, glyceryl triacetate, tributyl citrate, and glyceryl tripropionate.

6. The clear solid topical deodorant composition according to claim 2, wherein said one or more water-insoluble ester is a water-insoluble liquid ester.

7. The composition according to claim 2, wherein said optional ingredients are selected from the group consisting of coloring agents, fragrances, antimicrobial agents, topical anesthetics, topical analgesics, anti-oxidants, sunscreens, and insect repellents.

8. The clear solid topical deodorant composition according to claim 7 comprising 96% by weight of triethyl citrate, 3% by weight of dibenzylidine sorbitol, 0.25% by weight of a topical antimicrobial agent, and 0.75% by weight of fragrance.

9. The clear solid topical deodorant composition according to claim 7 comprising 50% by weight of triethyl citrate, 46.50% by weight of glyceryl tripropionate, 2.5% by weight of dibenzylidine sorbitol, and 1.00% by weight of fragrance.

10. A method of making a clear solid topical deodorant composition of claim 1 comprising:

forming a liquid phase comprising at least one water-insoluble ester of a water-soluble acid having solubility in water of less than 50% w/w at 20° C., said liquid phase being substantially free of water and of water-miscible solvents which are liquid at ambient temperature, and any optional ingredients;

heating said liquid phase to 100° C.;

slowly adding dibenzylidene sorbitol to said liquid phase with vigorous agitation;

agitating the resulting mixture for 10 to 30 minutes while maintaining the liquid phase temperature in the range of 100° to 140° C. until a clear solution results;

cooling said clear solution to 80° to 90° C. while stirring and adding any remaining ingredients; and pouring said clear solution into molds.

\* \* \* \* \*